United States Patent
Reddy et al.

(10) Patent No.: US 9,345,712 B2
(45) Date of Patent: May 24, 2016

(54) SOLID ORAL COMPOSITIONS OF TOLVAPTAN

(71) Applicant: HETERO RESEARCH FOUNDATION, Balangar, Hyderabad, Andhrapardesh (IN)

(72) Inventors: Bandi Parthasaradhi Reddy, Balanagar (IN); Podili Khadgapathi, Hyderabad (IN); Goli Kamalakar Reddy, Hyderabad (IN)

(73) Assignee: HETERO RESEARCH FOUNDATION (IN)

( * ) Notice: Subject to any disclaimer, the term of this patent is extended or adjusted under 35 U.S.C. 154(b) by 0 days.

(21) Appl. No.: 14/436,284

(22) PCT Filed: Oct. 23, 2013

(86) PCT No.: PCT/IN2013/000648
§ 371 (c)(1),
(2) Date: Apr. 16, 2015

(87) PCT Pub. No.: WO2014/068586
PCT Pub. Date: May 8, 2014

(65) Prior Publication Data
US 2015/0246053 A1    Sep. 3, 2015

(30) Foreign Application Priority Data
Oct. 31, 2012   (IN) ............................. 4536/CHE/2012

(51) Int. Cl.
*A61K 31/55*   (2006.01)
*A61K 9/20*    (2006.01)
*A61K 9/10*    (2006.01)

(52) U.S. Cl.
CPC . *A61K 31/55* (2013.01); *A61K 9/10* (2013.01); *A61K 9/2018* (2013.01); *A61K 9/2027* (2013.01); *A61K 9/2031* (2013.01); *A61K 9/2072* (2013.01); *A61K 9/2095* (2013.01)

(58) Field of Classification Search
CPC ...................................................... A61K 31/55
USPC ........................................................... 514/213
See application file for complete search history.

(56) References Cited

U.S. PATENT DOCUMENTS

2012/0207825 A1    8/2012   Roy et al.

FOREIGN PATENT DOCUMENTS

| CN | 102406622   | 4/2012 |
|----|-------------|--------|
| CN | 102406622 A | 4/2012 |
| EP | 2468258 A1  | 6/2012 |

OTHER PUBLICATIONS

International Search Report and Written Opinion; International Application No. PCT/IN13/00648; International Filing Date Oct. 23, 2013; Date of Mailing Jan. 14, 2015; 8 pages.

*Primary Examiner* — Taofiq A Solola
(74) *Attorney, Agent, or Firm* — Cantor Colburn LLP

(57) ABSTRACT

The present invention relates to solid dispersion compositions of tolvaptan and process for the preparation of oral dosage forms.

6 Claims, No Drawings

SOLID ORAL COMPOSITIONS OF TOLVAPTAN

PRIORITY

Cross-Reference to Related Applications

This patent application is a 371 of PCT/IN2013/000648 filed on Oct. 23, 2013, which claims the benefit of priority to Indian patent application number 4536/CHE/2012, filed on Oct. 31, 2012, under the provisions of 35 U.S.C. §119 and the International Convention for the Protection of Industrial Property, the contents herein are incorporated by reference herein in their entirety.

FIELD OF THE INVENTION

Disclosed herein are pharmaceutical compositions comprising tolvaptan or a pharmaceutically acceptable salt thereof.

Particularly, the invention relates to solid dispersion compositions of tolvaptan and process for preparing the same.

BACKGROUND

Tolvaptan is chemically described as (±)-4'-[(7-chloro-2,3,4,5-tetrahydro-5-hydroxy-1H-1-benzazepin-1-yl)carbonyl]-otolu-m-toluidide. Its empirical formula is $C_{26}H_{25}ClN_2O_3$, with structural formula as follows:

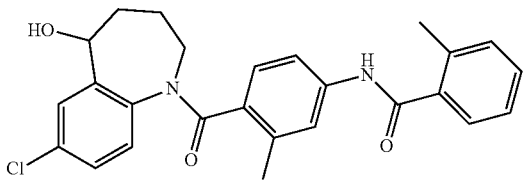 [SMILES: Cc1ccccc1C(=O)Nc1ccc(C(=O)N2CCCC(O)c3cc(Cl)ccc32)c(C)c1]

In the United States, tolvaptan is available as oral tablets containing 15 mg and 30 mg of tolvaptan, with trade name SAMSCA® by Otsuka America Pharmaceutical for the treatment of clinically significant hypervolemic and euvolemic hyponatremia.

U.S. Pat. No. 5,258,510 disclose tolvaptan.

U.S. Patent Application Publication No. 2010/0323006 A1 discloses process for the preparation of tolvaptan compositions by a method, comprising: 1) producing an amorphous composite from tolvaptan and hydroxypropyl cellulose; 2) mixing the amorphous composite obtained in step 1 with at least one member selected from the group consisting of low substituted hydroxypropylcellulose, carmellose, sodium carboxy methyl starch, and crospovidone; and 3) processing the mixture obtained in step 2 into a solid preparation.

Still, there is a need to develop alternative compositions of tolvaptan using simplified process. Accordingly, inventors of the present invention developed novel compositions of tolvaptan and process for preparing the same.

SUMMARY

The present invention relates to solid dispersion compositions comprising tolvaptan, a polymer and one or more pharmaceutically acceptable excipients:

In one embodiment solid dispersion composition comprise (a) tolvaptan or a pharmaceutically acceptable salt thereof and (b) a polymer selected from povidone; graft copolymer of polyethylene glycol, polyvinylcaprolactam and polyvinylacetate and combinations thereof.

Further embodiments describe solid dispersion techniques such as top spray granulation, hot melt extrusion, spray drying, co-precipitation and solvent evaporation for preparing compositions of the present invention.

Another embodiment of this invention relates to the process for preparation of tolvaptan composition by top spray granulation involving: (a) sifting one or more excipients followed by loading into fluid bed processor, (b) dissolving tolvaptan and at least one polymer in a solvent or mixture of solvents, (c) granulating the dry mix of step (a) by spraying the solution of step (b) onto it, (d) blending the granules of step (c) with extragranular excipients if any, followed by lubrication, and finally (e) compressing the lubricated blend of step (d) into tablets or filling into capsules.

Specific embodiment of this invention relates to pharmaceutical compositions prepared by top spray granulation (fluid bed granulation) comprising tolvaptan, povidone and one or more pharmaceutically acceptable excipients.

In yet another embodiment, this invention also relates to solid pharmaceutical compositions comprising tolvaptan or a pharmaceutically acceptable salt thereof; a polymer, a disintegrant, a solubilizing agent/surfactant, and one or more pharmaceutically acceptable excipients; wherein said composition is prepared by hot melt extrusion process:

Also included in the present invention is use of tolvaptan composition for treating hyponatremia.

DETAILED DESCRIPTION

The present invention relates to solid oral compositions comprising tolvaptan with one or more pharmaceutically acceptable excipients and process for their preparation.

The present invention in particular, relates to solid dispersion composition comprising tolvaptan, a polymer and one or more pharmaceutically acceptable excipients.

The term "tolvaptan" as used herein according to the present invention includes tolvaptan in the form of free base, a pharmaceutically acceptable salt thereof, amorphous tolvaptan, crystalline tolvaptan, any isomer, derivative, hydrate, solvate or prodrug or a combination thereof.

The term "composition" or "solid oral composition" or "dosage form" or "pharmaceutical composition" as used herein synonymously include solid dosage forms such as tablets, capsules, powder, particles, granules, pellets, minitablets and the like meant for oral administration.

A "composition" comprises an active pharmaceutical ingredient and at least one pharmaceutically acceptable excipient.

The term "active pharmaceutical ingredient" herein refers to tolvaptan or a pharmaceutically acceptable salt thereof.

The term "pharmaceutically acceptable excipient" includes a pharmaceutically acceptable material such as diluents, disintegrants, binders, lubricants, glidants, surfactants and the like, suitable for administering an active pharmaceutical ingredient. Each excipient should be "acceptable" in the sense of being compatible with the other ingredients of the formulation and not injurious to the patient.

As used in this specification and the appended claims, the singular forms "a", "an", and "the" include plural references unless the context clearly dictates otherwise. Thus for example, a reference to "a method" or "a process" includes one or more methods, one or more processes and/or steps of the type described herein and/or which will become apparent to those persons skilled in the art upon reading this disclosure and so forth.

Generally the pharmaceutical compositions of the present invention may be tablets, capsules or granules, specifically prepared as oral unit dosage form meant for immediate release.

Solid dispersion techniques as per the present invention includes top spray granulation (fluid bed granulation), hot melt extrusion, spray drying, melt agglomeration, co-precipitation, freeze drying, solvent evaporation, nitrogen stream, amorphous precipitation in crystalline matrix, supercritical fluid, eutectics or solid solution process.

In one aspect, the present invention relates to pharmaceutical composition prepared by a solid dispersion technique comprising (a) tolvaptan or a pharmaceutically acceptable salt thereof; and (b) a polymer selected from povidone; a graft copolymer comprised of polyethylene glycol, polyvinylcaprolactam and polyvinylacetate and combinations thereof.

In another aspect, this invention provides process for preparation of tolvaptan composition by top spray granulation comprises the steps of: (a) sifting one or more excipients followed by loading into fluid bed processor, (b) dissolving tolvaptan and at least one polymer in a solvent or mixture of solvents, (c) granulating the dry mix of step (a) by spraying the solution of step (b) onto it, (d) blending the granules of step (c) with extragranular excipients if any, followed by lubrication, and finally (e) compressing the lubricated materials of step (d) into tablets or filling into capsules.

Various useful polymers include but are not limited to povidone; a graft copolymer comprised of polyethylene glycol, polyvinylcaprolactam and polyvinylacetate (Soluplus®); copovidone; hydroxypropyl methylcellulose; poly (butyl methacrylate, (2-dimethyl aminoethyl) methacrylate, methyl methacrylate) 1:2:1 (Eudragit® E PO) and the like and combinations thereof.

In further aspect of the present invention, solvents suitable for processing the pharmaceutical compositions include one or more of organic solvents such as dichloromethane, ethanol, methanol, acetaldehyde, acetone, benzene, carbon disulphide, carbon tetrachloride, 1,2 dichloroethane, N,N-dimethylformamide, 1,4-dioxane, epichlorhydrin, ethyl acetate, ethyl ether, ethylene glycol, 2-ethoxyethanol (acetate), formaldehyde, isopropanol, methyl n-butyl ketone, methyl ethyl ketone, 2-methoxyethanol (acetate), perchloroethylene, toluene, 1,1,1-trichloroethane, trichloroethylene and the like, and combinations thereof; and aqueous solvents such as water.

In a specific embodiment the present invention relates to pharmaceutical compositions prepared by top spray granulation (fluid bed granulation) comprising tolvaptan, povidone and one or more pharmaceutically acceptable excipients.

Another aspect of this invention relates to solid pharmaceutical composition comprising tolvaptan or a pharmaceutically acceptable salt thereof; a polymer, a disintegrant, a solubilizing agent/surfactant, and one or more pharmaceutically acceptable excipients; wherein said composition is prepared by hot melt extrusion process.

Extruders suitable for processing the pharmaceutical compositions of the present invention include twin screw extruder, single screw extruder or intermeshing screw extruders, preferably twin screw extruder (Pharma HME 24) from Thermo Fisher Scientific.

In another aspect, this invention also provides pharmaceutical composition of tolvaptan prepared by hot melt extrusion process which comprises the steps of: (a) sifting and blending tolvaptan, a polymer and one or more excipients with a surfactant, (b) passing the materials of step (a) through hot melt extruder to form extrudes followed by milling, (c) blending the milled extrudes of step (b) with extra-granular excipients, followed by lubrication, and finally (d) compressing the lubricated materials of step (c) into tablets or filling into capsules.

In a further aspect, the ratio of tolvaptan to polymer in compositions of the present invention ranges between 1:0.1 to 1:4.

Pharmaceutically acceptable excipients according to the present invention selected from diluents, binders, disintegrants, solubilizing agents/surfactants, glidants, lubricants and combinations thereof.

Diluents: Various useful diluents include but are not limited to lactose, microcrystalline cellulose, starch, corn starch, pregelatinized starch, maize starch, potato starch, powdered celluloses, sorbitol, xylitol, dibasic calcium phosphate, calcium phosphate, calcium carbonate, magnesium carbonate and the like, and combinations thereof.

Binders: Various useful binders include but are not limited to hydroxypropyl cellulose, pregelatinized starch, powdered acacia, gelatin, guar gum, carbomers and the like, and combinations thereof.

Disintegrants: Various useful disintegrants include but are not limited to croscarmellose sodium, polacrilin potassium, sodium starch glycolate, crospovidone, pregelatinized starch, low substituted hydroxypropylcellulose and the like, and combinations thereof.

Solubilizing agents/Surfactants: Various useful solubilizing agents/surfactants include but are not limited to sorbitan mono laurate, sodium lauryl sulphate, polyoxyethylene-polyoxypropylene block copolymers (also known as poloxamers), polyethylene glycols, sodium stearyl sulfate, sodium oleyl sulfate, sodium cetyl sulfate, sodium dodecylbenzene sulfonate, dialkyl sodium sulfosuccinates, polysorbates and the like, and combinations thereof.

Glidants: One or more glidants, which improve the flow of a powder blend can be used. Useful glidants include but are not limited to, colloidal silicon dioxide, magnesium silicate, magnesium trisilicate, talc, and other forms of silicon dioxide, such as aggregated silicates and hydrated silica and the like, and combinations thereof.

Lubricants: Various useful lubricants include but are not limited to magnesium stearate, stearic acid, aluminium stearate, sucrose stearate, zinc stearate, sodium stearyl fumarate, talc, fumaric acid, palmitic acid, carnauba wax, hydrogenated vegetable oils, mineral oil and the like, and combinations thereof.

Also included in the present invention is use of tolvaptan compositions for treating hyponatremia.

EXAMPLES

The following examples further describe and demonstrate particular embodiments within the scope of the present invention. The examples are given solely for illustration and are not to be construed as limitations as many variations are possible without departing from spirit and scope of the invention.

Example 1

TABLE 1

Tablet compositions of Tolvaptan prepared by fluid bed top spray granulation method:

| Ingredients | Mg/Tab |
|---|---|
| Dry mix: | |
| Lactose monohydrate | 74.00 |
| Microcrystalline cellulose | 20.00 |
| Corn starch | 20.00 |
| Croscarmellose sodium | 9.00 |

TABLE 1-continued

Tablet compositions of Tolvaptan prepared by fluid bed top spray granulation method:

| Ingredients | Mg/Tab |
|---|---|
| Preparation of solution: | |
| Tolvaptan | 30.00 |
| Povidone | 15.00 |
| Dichloromethane | q.s. |
| Ethanol | q.s. |
| Extra-granular: | |
| Croscarmellose sodium | 14.70 |
| FD&C blue | 0.30 |
| Lubrication: | |
| Magnesium stearate | 2.00 |
| Total tablet weight | 185.00 |

Preparation Method
1. Lactose monohydrate, microcrystalline cellulose, corn starch and croscarmellose sodium were mixed in a fluid bed processor,
2. tolvaptan and povidone were dissolved in a mixture of dichloro methane and ethanol under continuous stirring to get a clear solution,
3. dry mix of step 1, was granulated by spraying the solution of step 2 onto it,
4. granules of step 3, were blended with extragranular croscarmellose sodium and FD&C blue,
5. blend of step 4, was lubricated with magnesium stearate, and finally
6. lubricated blend of step 5, was compressed into tablets.

Example 2

TABLE 2

Tablet compositions of Tolvaptan prepared by fluid bed top spray granulation method:

| Ingredients | Mg/Tab |
|---|---|
| Dry mix: | |
| Lactose monohydrate | 74.00 |
| Microcrystalline cellulose | 20.00 |
| Corn starch | 20.00 |
| Polacrilin potassium | 9.00 |
| Preparation of solution: | |
| Tolvaptan | 30.00 |
| Soluplus# | 15.00 |
| Dichloromethane | q.s. |
| Ethanol | q.s. |
| Extra-granular: | |
| Polacrilin potassium | 14.70 |
| FD&C blue | 0.30 |
| Lubrication: | |
| Magnesium stearate | 2.00 |
| Total tablet weight | 185.00 |

Soluplus#—a graft copolymer comprised of polyethylene glycol, polyvinylcaprolactam and polyvinylacetate.

Preparation Method
1. Lactose monohydrate, microcrystalline cellulose, corn starch and polacrilin potassium were mixed in a fluid bed processor,
2. tolvaptan and soluplus were dissolved in a mixture of dichloro methane and ethanol under continuous stirring to get a clear solution,
3. dry mix of step 1, was granulated by spraying the solution of step 2 onto it,
4. granules of step 3, were blended with extragranular polacrilin potassium and FD&C blue,
5. blend of step 4, was lubricated with magnesium stearate, and finally
6. lubricated blend of step 5, was compressed into tablets.

Comparative Example 3

TABLE 3

Tablet compositions of Tolvaptan prepared by wet granulation method:

| Ingredients | Mg/Tab |
|---|---|
| Dry mix: | |
| Tolvaptan | 30.00 |
| Lactose monohydrate | 70.01 |
| Microcrystalline cellulose | 47.75 |
| Corn starch | 10.00 |
| Croscarmellose sodium | 22.90 |
| FD&C blue | 0.34 |
| Preparation of binder solution: | |
| Povidone | 2.00 |
| Purified water | q.s. |
| Lubrication: | |
| Magnesium stearate | 2.00 |
| Total tablet weight | 185.00 |

Preparation Method
1. Tolvaptan, lactose monohydrate, microcrystalline cellulose, corn starch, croscarmellose sodium and FD&C blue were sifted,
2. binder solution was prepared using povidone and purified water,
3. sifted materials of step 1, were loaded into rapid mixer granulator and granulated using binder solution of step 2,
4. the wet mass of step 3 was dried and milled to get the desired granules,
5. granules of step 4 were lubricated with magnesium stearate,
6. lubricated granules of step 5 were compressed into tablets using suitable punches.

Example 4

TABLE 4

Tablet compositions of Tolvaptan prepared by hot melt extrusion process:

| Ingredients | Mg/Tab |
|---|---|
| Tolvaptan | 30.00 |
| Soluplus# | 90.00 |
| Sorbitan monolaurate (Span 20) | 3.00 |
| Extra-granular: | |
| Lactose monohydrate | 31.70 |
| Croscarmellose sodium | 28.00 |
| FD&C blue | 0.30 |
| Lubrication: | |
| Magnesium stearate | 2.00 |
| Total tablet weight | 185.00 |

Soluplus#—a graft copolymer comprised of polyethylene glycol, polyvinylcaprolactam and polyvinylacetate.

Preparation Method:
1. Tolvaptan, Soluplus® were blended with sorbitan mono laurate in a high shear mixer,
2. blend of step 1, was fed into an extruder, and the resulted extrudes were milled,
3. milled extrudes of step 2, were blended with lactose monohydrate, croscarmellose sodium and FD&C blue,
4. blend of step 3, was lubricated with magnesium stearate, and finally compressed into tablets.

Example 5

TABLE 5

Tablet compositions of Tolvaptan prepared by hot melt extrusion process:

| Ingredients | Mg/Tab |
| --- | --- |
| Tolvaptan | 30.00 |
| Copovidone | 90.00 |
| Sorbitan mono laurate (Span 20) | 3.00 |
| Extra-granular: | |
| Lactose monohydrate | 31.70 |
| Polacrilin potassium | 28.00 |
| FD&C blue | 0.30 |
| Lubrication: | |
| Magnesium stearate | 2.00 |
| Total tablet weight | 185.00 |

Preparation Method
1. Tolvaptan, copovidone were blended with sorbitan mono laurate in a high shear mixer,
2. blend of step 1, was fed into an extruder, and the resulted extrudes were milled,
3. milled extrudes of step 2, were blended with lactose monohydrate, polacrilin potassium and FD&C blue,
4. blend of step 3, was lubricated with magnesium stearate, and finally compressed into tablets or alternatively filled into capsules.

Comparative Study on Dissolution Time:

Dissolution test was performed for tablets prepared as per the Example 1 and Comparative example 3, using. USP apparatus type II, at 100 rpm, in 900 ml of purified water with 1% sodium lauryl sulphate.

TABLE 6

Comparative study on dissolution time:

| | Time in minutes | | | | | |
| --- | --- | --- | --- | --- | --- | --- |
| | 5 min | 10 min | 20 min | 30 min | 45 min | 60 min |
| Example-1 (fluid bed top spray granulation) | 92 | 96 | 97 | 98 | 98 | 98 |
| Comparative example 3 (wet granulation) | 45 | 58 | 68 | 73 | 79 | 83 |

Based on the results presented in Table 6, tolvaptan compositions prepared by fluid bed top spray granulation (Example-1) showed improved dissolution properties as compared to compositions prepared by conventional wet granulation (Comparative example 3).

We claim:
1. A solid dispersion composition comprising
   (a) tolvaptan or a pharmaceutically acceptable salt thereof and
   (b) povidone, wherein the ratio of tolvaptan to povidone is 1:0.1 to 1:0.5.
2. A method of preparing the solid dispersion composition according to claim 1, using top spray granulation, hot melt extrusion, spray drying, co-precipitation or solvent evaporation to prepare the solid dispersion.
3. The method of claim 2, wherein the solid dispersion is prepared by top spray granulation.
4. The composition according to claim 1, further comprising one or more excipients selected from diluents, disintegrants, binders, lubricants, glidants and surfactants.
5. The composition of claim 1 in the form of a tablet, granules or a capsule.
6. The method of claim 3, wherein the solid dispersion is prepared by:
   (a) sifting one or more excipients followed by loading into a fluid bed processor to form a dry mix,
   (b) dissolving tolvaptan and povidone in a solvent mixture of methylene chloride and methyl alcohol to form a solution,
   (c) granulating the dry mix of step (a) by spraying the solution of step (b) onto it to form granules,
   (d) blending the granules of step (c) with optional extra-granular excipients, followed by lubrication to provide a lubricated blend, and
   (e) compressing the lubricated blend of step (d) into tablets or filling the lubricated blend into capsules.

* * * * *